United States Patent [19]

Pews et al.

[11] Patent Number: 5,041,674
[45] Date of Patent: Aug. 20, 1991

[54] PROCESS AND INTERMEDIATES FOR THE PREPARATION OF 2,6-DIFLUOROANILINE

[75] Inventors: R. Garth Pews, Midland; James A. Gall, Sanford, both of Mich.

[73] Assignee: DowElanco, Indianapolis, Ind.

[21] Appl. No.: 537,975

[22] Filed: Jun. 14, 1990

[51] Int. Cl.$^5$ .................. C07C 211/46; C07C 209/22
[52] U.S. Cl. ................................. 564/442; 568/938; 570/127
[58] Field of Search .................. 568/938; 564/442; 570/127

[56] References Cited

U.S. PATENT DOCUMENTS

| | | | |
|---|---|---|---|
| 2,519,317 | 8/1950 | Koika et al. | 568/938 X |
| 3,546,293 | 12/1970 | Kalopissis et al. | 564/442 |
| 4,229,365 | 10/1980 | Oeser et al. | 568/938 X |
| 4,868,347 | 9/1989 | Blank et al. | 568/937 |

Primary Examiner—Catherine S. Kilby Scalzo
Attorney, Agent, or Firm—Craig E. Mixan; Ronald G. Brookens

[57] ABSTRACT

1-Chloro-3,5-difluorobenzene is chlorinated to give 4,6-difluoro-1,2,3-trichlorobenzene which in turn is nitrated and reduced to the corresponding novel aniline, 2,6-difluoro-3,4,5-trichloroaniline. Further reduction of this aniline provides 2,6-difluoroaniline with high selectivity.

3 Claims, No Drawings

PROCESS AND INTERMEDIATES FOR THE PREPARATION OF 2,6-DIFLUOROANILINE

FIELD OF INVENTION

The present invention concerns a process for preparing 2,6-difluoroaniline from 1-chloro-3,5-difluorobenzene which is characterized by the steps of chlorination, nitration and reduction.

BACKGROUND OF THE INVENTION 2,6-Difluoroaniline is useful as an intermediate in the manufacture of a variety of chemical products including, for example, dyes, pharmaceuticals and agricultural chemicals, and is presently manufactured in a multistep process involving the following reaction sequence:

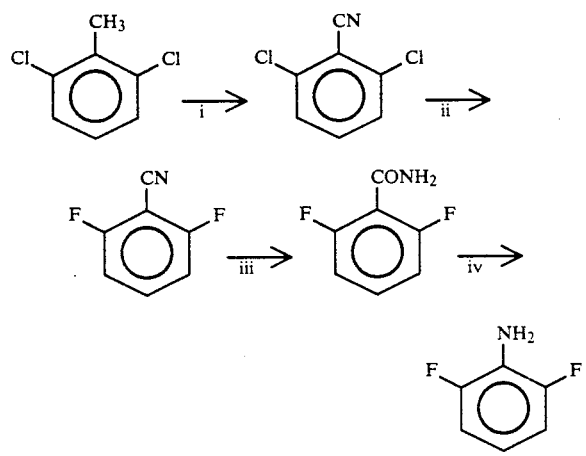

i) ammoxidation of 2,6-dichlorotoluene to 2,6-dichlorobenzonitrile;
ii) halogen-exchange to 2,6-difluorobenzonitrile;
iii) hydration to 2,6-difluorobenzamide; and
iv) Hoffman rearrangement to 2,6-difluoroaniline.

In addition, 2,6-dichlorotoluene itself is not readily available. Thus, as a result of the complexities of the chemistry, although commercially available, 2,6-difluoroaniline is quite expensive.

Alternative technologies have been suggested to manufacture 2,6-difluoroaniline, but they also have serious drawbacks. For example, fluorinated aromatics are often prepared by diazonium chemistry in which an amino moiety is transformed into a fluorine substituent by reaction with nitrous acid to form a diazonium salt and subsequent decomposition of the diazonium salt in the presence of fluoride. However, diazonium salts are unstable and the decomposition reaction is highly exothermic. In addition, the decompositions are generally conducted in highly reactive and corrosive anhydrous hydrofluoric acid.

Alternatively, 2,6-difluoroaniline has also been prepared via lithiation of 1,3-difluorobenzene followed by carbonation to the carboxylic acid and conversion of the acid moiety to the amine with hydrazoic acid (see British Patent 1,080,167). Unfortunately, neither lithiation nor hydrazoic acid lend themselves to large scale use.

Thus, it is desirable to have a process for safely and economically producing 2,6-difluoroaniline in good yield from readily available starting materials.

SUMMARY OF THE INVENTION

The present invention concerns a process for preparing 2,6-difluoroaniline from 1-chloro-3,5-difluorobenzene by the following reaction scheme:

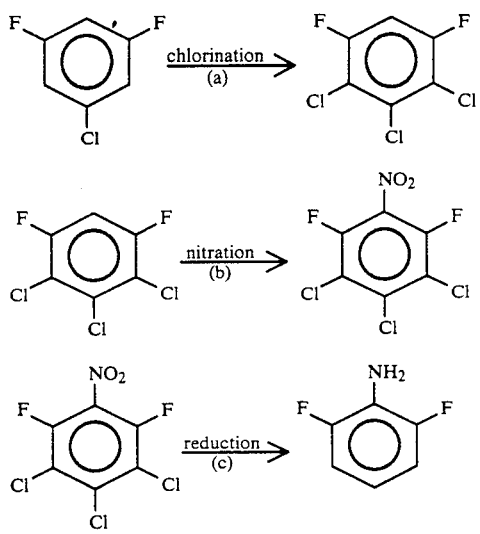

According to the present invention, the improved process is comprised of the following steps:
(a) chlorinating 1-chloro-3,5-difluorobenzene to give 4,6-difluoro-1,2,3-trichlorobenzene;
(b) nitrating the 4,6-difluoro-1,2,3-trichlorobenzene to give 2,6-difluoro-3,4,5-trichloronitrobenzene; and
(c) reducing the 2,6-difluoro-3,4,5-trichloronitrobenzene to give 2,6-difluoroaniline.

By selectively chlorinating the 2- and 6-positions in 1-chloro-3,5-difluorobenzene to give 4,6-difluoro-1,2,3-trichlorobenzene, a nitro group can then be introduced into the only remaining position between the two fluoro substituents with a high degree of selectivity. The concomitant hydrogenation of the ring chlorine atoms with the nitro group leads directly to the desired 2,6-difluoroaniline.

The selective chlorination process is another embodiment of the present invention as are the intermediate compounds of the formula

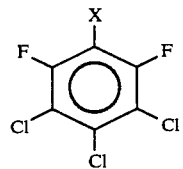

wherein
X is —NO₂ or —NH₂.

DETAILED DESCRIPTION OF THE INVENTION

The 1-chloro-3,5-difluorobenzene starting material is a known compound and, although not commercially available, it can be readily prepared by a partial fluorine exchange reaction on 1,3,5-trichlorobenzene; see R. H. Shiley et al., *J. Fluorine Chem.*, 2, 19 (1972–1973).

4,6-Difluoro-1,2,3-trichlorobenzene is prepared by contacting 1-chloro-3,5-difluorobenzene with chlorine in the presence of a metal halide catalyst and a solvent. The chlorination generally produces a mixture of compounds to which 1, 2 or 3 chlorines have been added:

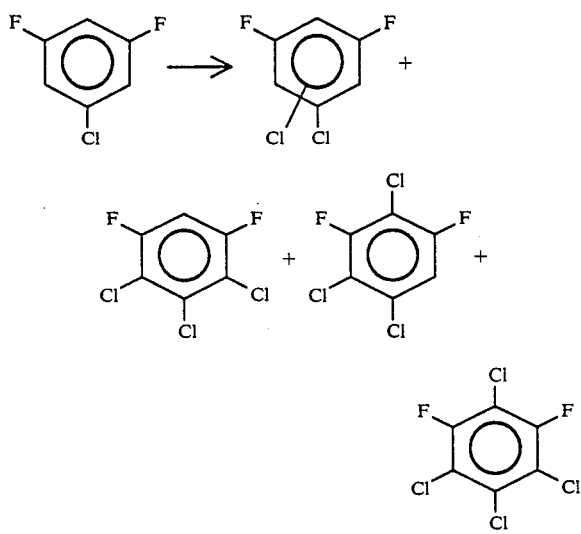

By controlling reaction conditions, such as temperature and the amount and rate of chlorine added, so that dichlorination predominates, mixtures consisting of up to 70–80 percent of the desired 4,6-difluoro-1,2,3-trichlorobenzene are unexpectedly obtained.

By metal halide catalyst is meant any of the Lewis acid catalysts typically employed in electrophilic aromatic halogenation reactions. The metal halide catalysts include but are not limited to compounds of the formula $$M^nX_n$$

wherein

M is aluminum (Al,), boron (B), iron (Fe), antimony (Sb), tin (Sn) or titanium (Ti);

X is chloro, bromo or fluoro; and n is an integer which is the oxidation state of the metal.

Preferably, M is aluminum, iron or antimony and X is chloro. For aluminum, iron and antimony, n is preferably 3. Catalysts which can conveniently be employed include: aluminum chloride, aluminum bromide, boron trifluoride, iron chloride, titanium chloride, antimony chloride and the like. Aluminum chloride and iron chloride are usually preferred.

The metal halide catalyst is used in amounts of from about 0.1 to about 20 weight percent of the 1-chloro-3,5-difluorobenzene initially charged. Catalyst levels in the range of from 1.0 to 10 weight percent are generally preferred. The metal halide catalyst should be maintained anhydrous or as water-free as possible, since water can chemically react and deactivate the catalyst.

Contacting of the ingredients is performed in the presence of a solvent which is resistant or inert to chlorination. Such resistant or inert solvents include, but are not limited to, chlorinated aliphatic hydrocarbons such as methylene chloride, carbon tetrachloride, chloroform, perchloroethylene, 1,2-dichloroethane, trichloroethylene and the like. The solvent can be employed in an amount sufficient to at least slurry the ingredients up to any amount which would homogenize the ingredients. Typically, the concentration of the 1-chloro-3,5-difluorobenzene is from about 5 to about 50 percent by weight of a solution containing a resistant or inert solvent; preferably from about 10 to about 25 percent by weight.

By controlling temperatures, pressures, and the amounts and rates of chlorine added so that dichlorination predominates, mixtures consisting of high proportions of 4,6-difluoro-1,2,3-trichlorobenzene as opposed to 3,5-difluoro-1,2,4-trichlorobenzene are obtained. The temperature can range from about −20° to about 85° C., preferably from about 0° to about 30° C. to limit overchlorination. Although superatmospheric pressures can be employed and are often preferred for maintaining contact between the gaseous chlorine and the liquid reaction mixture, operation at atmospheric pressure is often more convenient. The times for contacting the ingredients can vary, ranging from 15 minutes (min) to about 24 hours or more depending upon the temperature, pressure and addition rate of the chlorine. Depending upon the reaction conditions some of the chlorine added may bubble through the reaction mixture and be lost to reaction. Preferably the chlorine should be added at a rate commensurate with its reaction rate. In any case, enough chlorine should be added so that each mole of 1-chloro-3,5-difluorobenzene reacts with from about 1.8 to about 2.2 moles of chlorine.

In a typical chlorination reaction, the starting material, solvent and catalyst are mixed at the appropriate temperature and chlorine is slowly introduced into the reaction mixture until the desired degree of chlorination has been achieved. Reaction progress can be conveniently monitored by gas chromatography. After completion of the reaction, the mixture is worked-up by conventional techniques, such as, for example, extraction. The desired 4,6-difluoro-1,2,3-trichlorobenzene can be separated from the reaction mixture by conventional procedures, such as distillation or column chromatography; however, it is often easier to nitrate the reaction mixture before workup and to make the separation at a later stage of the process.

2,6-Difluoro-3,4,5-trichloronitrobenzene is prepared by contacting 4,6-difluoro-1,2,3-trichlorobenzene with a nitrating agent. It is often convenient to perform the nitration directly on the reaction mixtures obtained from the chlorination of 1-chloro-3,5-difluorobenzene.

Normally a variety of reagents can be used to effect nitration but, since pentahalobenzenes are relatively unreactive to electrophilic aromatic substitutions, it is necessary to use a relatively powerful nitrating agent. The desired nitration can be conveniently accomplished in mixed acid media, i.e., nitric acid-sulfuric acid mixtures. It is desirable to maintain the amount of water in the mixed acid media below about 10 percent to ensure that most of the nitric acid remains ionized as nitronium ion ($\oplus NO_2$). Thus the mixed acid media can be conveniently prepared from concentrated sulfuric acid (96 percent) and from fuming nitric acid (90 percent). Oleum or fuming sulfuric acid may be advantageously used in place of the concentrated sulfuric acid. Generally, in preparing the mixed acid media, from 1 to 10 parts by weight of sulfuric acid are employed for each part by weight of nitric acid; from 1.5 to 4 parts by weight of sulfuric acid for each part by weight nitric acid are preferred. At least a stoichiometric amount of nitric acid to substrate is required. Since only one position on the substrate is susceptible to nitration, overnitration is not a concern and the use of 2 to 5 fold excesses and more of nitric acid are preferred.

The contacting of the mixed acid and 4,6-difluoro-1,2,3-trichlorobenzene is generally performed in the absence of a solvent. Thus, when reaction mixtures obtained from the chlorination of 1-chloro-3,5-difluorobenzene are nitrated directly, removal of the chlorination solvent prior to nitration is preferred. This can conveniently be done by adding the sulfuric acid component of the mixed acid media to the chlorination reaction mixture and then removing the solvent by distillation.

The nitrations are generally conducted at temperatures between room temperature and 50° C. For convenience and safety, operation at ambient temperature and atmospheric pressure is usually preferred. Because the nitration mixture is a multiphase system, very efficient agitation is required.

In a typical nitration reaction, in which the chlorination mixture containing 4,6-difluoro-1,2,3-trichlorobenzene is used directly, sulfuric acid is carefully added to the crude chlorination mixture and the solvent is removed by distillation. The nitric acid is carefully added and the reaction mixture is stirred at ambient temperature until the reaction is complete. The product can be isolated by conventional procedures. For example, the reaction mixture can be quenched in ice water and the product mixture can be obtained by extraction. 2,6-Difluoro-3,4,5-trichloronitrobenzene may be isolated from the crude product mixture by conventional procedures such as column chromatography or the crude product mixture can itself be reduced and separation postponed until the aniline stage.

In the reduction step, the 2,6-difluoro-3,4,5-trichloronitrobenzene is reacted with hydrogen in the presence of a supported metal hydrogenation-catalyst. During the course of the reaction, the nitro group is first converted to an amine and the chlorines are then selectively replaced by hydrogen. By a supported metal hydrogenation-catalyst is meant any metal catalyst on a variety of supports that effects both the reduction of the nitro group and the aromatic chlorine substituents. Platinum and palladium are particularly well suited for this application. Typical supports include silica, alumina, magnesia and carbon. The preferred catalyst is palladium supported, for example, on carbon. The most preferred catalysts range from about 0.5 to about 10 weight percent palladium on carbon. Generally, from about 0.001 to about 0.05 parts of platinum or palladium are employed per part of difluorotrichloronitrobenzene; from about 0.01 to about 0.03 parts are preferred.

The reduction is conveniently conducted with an excess of hydrogen. For example, hydrogen gas can be continuously sparged into the reaction mixture at atmospheric pressure or a sealed reactor can be pressurized with hydrogen gas.

The reduction is generally performed in an organic solvent which is inert to the reaction conditions. Alcohols, such as, for example, methanol, ethanol and propanol are particularly preferred.

The reduction is generally carried out at a temperature from about ambient to about 150° C., preferably from ambient to about 85° C. Operating pressures are not critical and may vary from atmospheric pressure to about 700 pounds per square inch gauge (psig). Pressures from atmospheric to about 200 psig are preferred.

The reduction can be carried out all at once or in stages. If desired, the intermediate 2,6-difluoro-3,4,5-trichloroaniline may be isolated after the initial reduction of the nitro group. Since the reduction of the aromatic chlorines produces hydrogen chloride, at least one equivalent of an HCl acceptor should be added for each chlorine reduced to buffer the system. The use of acetate as the buffer is preferred.

In a typical reduction reaction, in which a nitration mixture containing both 2,4-difluoro-3,5,6-trichloronitrobenzene and 2,6-difluoro-3,4,5-trichloronitrobenzene is used directly, the crude nitrobenzenes are introduced into a pressure reactor along with an alcohol such as set forth herein above and a supported metal hydrogenation-catalyst. The reactor is sealed, pressurized with hydrogen and stirred until the nitro group has been converted to an amine. A buffer is then added and the reactor is repressurized with hydrogen and stirred at 65°-85° C. until the chloro substituents have been removed from the benzene ring. After cooling and venting, the mixture of anilines is isolated by conventional procedures such as filtration and extraction. By virtue of their 16°-18° C. boiling point difference, the resulting mixture of 2,4-difluoroaniline and 2,6-difluoroaniline can be conveniently and effectively separated by fractional distillation.

The following examples are presented to illustrate the invention and should not be construed as limiting the scope of the invention. All melting points and boiling points are uncorrected.

EXAMPLE A:

Preparation of 1-Chloro-3,5-Difluorobenzene Starting Material

To a 300 milliliter (mL) pressure reactor was added 18.2 grams (g) (0.1 moles) of 1,3,5-trichlorobenzene, 100 mL of 1,3-dimethyl-2-imidazolidinone (solvent), 5.0 g of 1,3-diethylbenzene (internal standard) and 12.76 g (0.22 moles) of potassium fluoride which had been previously dried for 24 hours (hr) at 150° C. The reactor was sealed and pressure tested with nitrogen. The reaction mixture was heated with stirring for 12 hr. Upon completion of the reaction, the reactor was cooled and the contents analyzed by gas chromatography. The results of a series of reactions are summarized in Table I.

The product from these runs was purified by distillation using a concentric tube distillation column. 1-Chloro-3,5-difluorobenzene had a boiling point of 115°-116° C: mass spec.: 148. 1,3-Dichloro-5-fluorobenzene had a boiling point of 158°-160° C.; mass spec.: 164.

TABLE I

FLUORINATION of 1,3,5-TRICHLOROBENZENE

TCB + KF →(12 hr) DCFB + DFCB + TFB

| REACTANTS (mol) | GC ANALYSIS (mol-Area %) |
| --- | --- |

TABLE I-continued

| RUN | TEMP °C. | KF | TCB | TCB | DCFB | DFCB | TFB |
|---|---|---|---|---|---|---|---|
| 1 | 230 | 0.22 | 0.10 | 0.051 | 0.050 | 0.008 | 0.001 |
| 2 | 250 | 0.22 | 0.10 | 0.002 | 0.025 | 0.045 | 0.006 |
| 3 | 250 | 0.22 | 0.10 | 0.008 | 0.049 | 0.037 | 0.004 |
| 4 | 260 | 0.22 | 0.10 | 0.002 | 0.031 | 0.055 | 0.010 |
| 5 | 270 | 0.22 | 0.10 | 0.000 | 0.015 | 0.060 | 0.019 |
| 6 | 280 | 0.22 | 0.10 | 0.000 | 0.019 | 0.054 | 0.013 |
| 7 | 300 | 0.66 | 0.10 | 0.000 | 0.000 | 0.019 | 0.062 |
| 8 | 300 | 0.60 | 0.10 | 0.000 | 0.000 | 0.004 | 0.075 |

EXAMPLE 1

Preparation of 4,6-Difluoro-1,2,3-Trichlorobenzene

To a 250 mL, 3-necked, round bottom flask equipped with a condenser, caustic scrubber, thermometer, magnetic stirrer and chlorine sparge tube was added 14.8 g (0.1 moles) of 1-chloro-3,5-difluorobenzene, 150 mL of ethylene dichloride (EDC) and 1.34 g (10 mole percent) of aluminum chloride. The flask was cooled to 10° C. and 22 g of chlorine gas was slowly bubbled into the flask for the reaction to reach completion. The reaction mixture was poured over ice and the organic layer was separated, dried over magnesium sulfate and filtered. The solvent was removed under reduced pressure to give 19.6 g (0.091 moles) of product mixture having the following composition: 4% dichlorodifluorobenzenes (mass spec: 182); 18% 2,6-difluoro-1,3,4-trichlorobenzene (mass spec: 216): 74% 4,6-difluoro-1,2,3-trichlorobenzene (mass spec: 216); and 4% 4,6-difluoro-1,2,3,5-tetrachlorobenzene (mass spec: 250).

EXAMPLE 2

Preparation of 2,6-Difluoro-3,4,5-Trichloronitrobenzene

To a 250 mL, 3-necked, round bottom flask equipped with condenser, caustic scrubber, thermometer, magnetic stirrer and addition funnel, was added 52 g of conc. sulfuric acid followed dropwise by 39.2 g of 90% nitric acid. The difluorotrichlorobenzene mixture from Example 1 was added dropwise over 2 hr and the reaction mixture was stirred at ambient temperature for 3 hr. After completion of the reaction, the mixture was poured onto ice and the organics were extracted with methylene chloride. After drying over magnesium sulfate and filtration, the solvent was evaporated under reduced pressure to give 19.7 g (0.075 moles) of product mixture having the following composition: 65% 2,6-difluoro-3,4,5-trichloronitrobenzene (mass spec: 261); 19% 2,4-difluoro-3,5,6-trichloronitrobenzene (mass spec: 261); 11% 4,6-difluoro-1,2,3,5-tetrachlorobenzene: and 5% other impurities.

The crude nitration product was purified by elution with 90:10 hexane-benzene from a silica gel column. Removal of the solvent under reduced pressure gave a solid product, melting point 33°-35° C.

EXAMPLE 3

Preparation of 2,6-Difluoro-3,4,5-Trichloronitrobenzene Using Ferric Chloride Catalyst To a 500 mL, 3-necked, round bottom flask equipped with condenser, caustic scrubber, thermometer, magnetic stirrer and chlorine sparge tube was added 20 g (0.135 moles) of 1-chloro-3,5-difluorobenzene, 200 mL of methylene chloride and 1.32 g (10 mole %) of ferric chloride. The flask was cooled to 10° C. and 50 g of chlorine was added in increments of 10-20 g over 4 hr. The chlorine sparge tube was replaced with an addition funnel and 92.6 g of conc. sulfuric acid was slowly added dropwise. The addition funnel was replaced with a distillation head and the methylene chloride was removed by distillation. The distillation head was replaced by the addition funnel and 58.9 g of 90% nitric acid was added dropwise. The reaction mixture was stirred at ambient temperature for 3 hr and then quenched in ice water. The organics were extracted with methylene chloride and dried over magnesium sulfate. The methylene chloride was removed under reduced pressure to give 29.6 g of product mixture having the following composition: 8% 4,6-difluoro-1,2,3,5-tetrachlorobenzene; 20% 2,4-difluoro-3,5,6-trichloronitrobenzene; and 72% 2,6-difluoro-3,4,5-trichloronitrobenzene.

EXAMPLE 4

Preparation of 2,6-Difluoro-3,4,5-Trichloronitrobenzene Using Antimony Trichloride Catalyst The procedure of Example 3 was repeated substituting 3.0 g (10 mole %) of antimony trichloride as the catalyst. The chlorination was conducted at ambient temperature over 42 hr by incrementally adding about 90 g of chlorine. After nitration, workup gave 26.3 g of product mixture having the following composition: 3% 4,6-difluoro-1,2,3,5-tetrachlorobenzene; 18% 2,4-difluoro-3,5,6-trichloronitrobenzene and 76% 2,6-difluoro-3,4,5-trichloronitrobenzene.

EXAMPLE 5

Preparation of 2,6-Difluoro-3,4,5-Trichloronitrobenzene Using Aluminum Chloride Catalyst The procedure of Example 3 was repeated using 22.8 g (0.154 moles) of 1-chloro-3,5-difluorobenzene, 30 g of chlorine, 105.6 g of conc. sulfuric acid and 58.6 g of 90% nitric acid and substituting 0.61 g (3 mole %) of aluminum chloride as the catalyst. The chlorination was conducted at 3° C. and the nitration at room temperature. Product workup gave 36 g of product mixture having the following composition: 2% 4,6-difluoro-1,2,3-trichlorobenzene; 19% 2,4-difluoro-3,5,6-trichloronitrobenzene; 69% 2,6-difluoro-3,4,5-trichloronitrobenzene; and 7% 4,6-difluoro-1,2,3,5-tetrachlorobenzene.

EXAMPLE 6

Preparation of 2,6-Difluoro-3,4,5-Trichloroaniline

To a 45 mL Hastelloy "C" pressure reactor was added 4.5 g of 2,6-difluoro-3,4,5-trichloronitrobenzene, 0.91 g of 10 percent palladium on charcoal and 25 mL of iso-propyl alcohol. The reactor was purged with nitrogen, sealed and pressurized to 130 psig with hydrogen. After stirring at ambient temperature for 5 hrs, the reactor was vented. The catalyst was removed by filtration and the solvent was evaporated under reduced pressure to give 3.7 g of solid product having a mp 137°-140° C. The IR, Mass and NMR spectra were consistent with the structure.

EXAMPLE 7

Preparation of 2,6-Difluoroaniline

To a 600 mL Hastelloy "C" pressure reactor was added 26.3 g (0.1 moles) of a mixture containing 76 percent 2,6-difluoro-3,4,5-trichloronitrobenzene, 18 percent 2,4-difluoro-3,5,6-trichloronitrobenzene and 3 percent 4,6-difluoro-1,2,3,5-tetrachlorobenzene, 200 mL of methanol and 2.63 g of 10 percent palladium on charcoal. The reactor was sealed and pressurized to 150 psig with hydrogen. After stirring 16 hr at ambient temperature, the reactor was vented. Gas chromatographic analysis indicated complete conversion of the nitro group to the amine. Sodium acetate (33.1 g; 0.4 moles) was added to the mixture and the reactor was resealed and pressurized to 150 psig with hydrogen. After stirring at 80° C. for 6 hr, the reactor was cooled and vented. The solids were removed by filtration and the methanol was removed by distillation using a concentric tube column. The residue was diluted with methylene chloride and the organic phase was washed with water to remove methanol and acetic acid. The organics were dried over magnesium sulfate and filtered, and the solvent was evaporated to give 9.6 g (0.074 moles) of liquid containing 89 percent 2,6-difluoroaniline and 11 percent 2,4-difluoroaniline.

EXAMPLE 8

Preparation of 2,6-Difluoroaniline

To a 600 mL Hastelloy "C" pressure reactor was added 29.6 g (0.113 moles) of crude difluorotrichloronitrobenzene mixture, 300 mL of iso-propyl alcohol and 6.03 g of 10 percent palladium on charcoal. The reactor was sealed and pressurized to 150 psig with hydrogen. The reaction mixture was stirred at ambient temperature for 5 hr while hydrogen was added as needed. After the nitro group was reduced to the amine, the reaction mixture was transferred to a 500 mL 3-necked flask equipped with condenser, nitrogen sparge tube, thermometer and mechanical stirrer. Sodium formate (46.1 g) was added and the mixture was refluxed for 70 hr. After cooling, the solids were removed by filtration and the iso-propyl alcohol was removed by distillation. The organics were diluted with methylene chloride, washed with water and dried over magnesium sulfate. Evaporation of the solvent gave 8.0 g of a difluoroaniline mixture having a 2,6- to 2,4-isomer ratio of 2.3.

EXAMPLE 9

Preparation of 2,6-Difluoroaniline

To a 500 mL 3-necked flask equipped with a condenser, caustic scrubber, thermometer, magnetic stirrer and chlorine sparge tube was added 29.7 g (0.2 moles) of 1-chloro-3,5-difluorobenzene, 250 mL of methylene chloride and 5 mole percent of aluminum chloride catalyst. The reaction mixture was cooled to 10° C. and chlorine was slowly added until about 1.9 equivalents of chlorine had been added. The sparge tube was removed and replaced with an addition funnel. Conc. sulfuric acid (140 g) was added dropwise and the addition funnel was replaced with a distillation head. The methylene chloride was distilled and the pot cooled to room temperature. The distillation head was replaced with an addition funnel and 80 g of 90 percent nitric acid was added dropwise. The reaction mixture was stirred at room temperature for 1½ hr and was poured over ice. The organics were extracted with methylene chloride and dried over magnesium sulfate. After filtration, the solvent was evaporated to give 47.5 g of a mixture containing 10 percent difluorodichlorobenzene, 73 percent of 2,6-difluoro-3,4,5-trichloronitrobenzene and 17 percent of 2,4-difluoro-3,5,6-trichloronitrobenzene.

To a 600 mL Hastelloy "C" pressure reactor was added the above mixture (47.5 g), 300 mL of methanol and 4.75 g of 10 percent palladium on charcoal. The reactor was flushed with nitrogen, sealed and pressurized to 150 psig with hydrogen. After 16 hr at room temperature, the reactor was vented and 66 g of sodium acetate were added. The reactor was resealed, pressurized to 150 psig with hydrogen and heated at 80° C. for 6 hr. The reactor was cooled and vented. The solids were removed from the reaction mixture by filtration and the methanol was removed by distillation. The residue was diluted with methylene chloride and the organics were washed with water to remove methanol and acetic acid. The organics were dried over magnesium sulfate and filtered, and the solvent was evaporated to give 16.8 g of a difluoroaniline mixture having a 2,6- to 2,4-isomer ratio of 4.0.

The reaction mixture was carefully distilled at atmospheric pressure and about 10 g of 2,6-difluoroaniline of about 98 percent purity was collected boiling between 150°-154° C.

What is claimed is:

1. A process for preparing 2,6-difluoroaniline which comprises the following steps:
   (a) chlorinating 1-chloro-3,5-difluorobenzene to produce 4,6-difluoro-1,2,3-trichlorobenzene;
   (b) nitrating the 4,6-difluoro-1,2,3-trichlorobenzene to produce 2,6-difluoro-3,4,5-trichloronitrobenzene; and
   (c) reducing the 2,6-difluoro-3,4,5-trichloronitrobenzene to produce 2,6-difluoroaniline.

2. A process for preparing 4,6-difluoro-1,2,3-trichlorobenzene which comprises contacting 1-chloro-3,5-difluorobenzene with a sufficient amount of chlorine so as to incorporate from 1.8 to 2.2 equivalents of chlorine per aromatic ring in the presence of a metal halide catalyst in a chlorinated aliphatic hydrocarbon solvent at a temperature from about 0° to about 30° C.

3. A compound of the formula

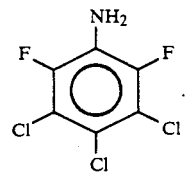

* * * * *